March 17, 1936. J. DE VINK Plant Pat. 169
ROSE
Filed Oct. 18, 1935
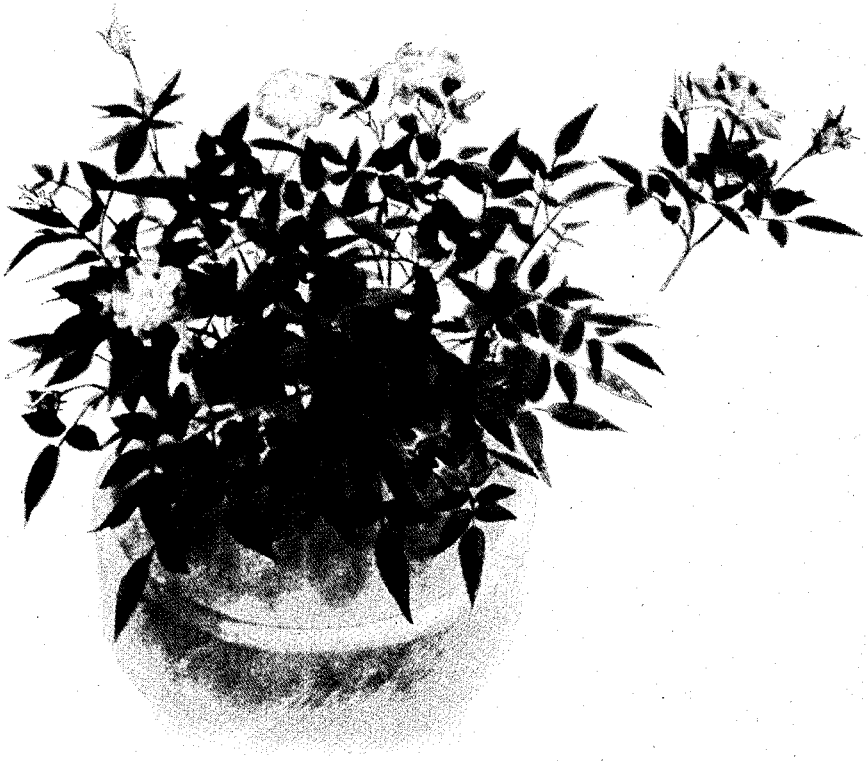
Inventor
John de Vink
By Robert Robb
Attorneys Patented Mar. 17, 1936

UNITED STATES PATENT OFFICE

169

ROSE

John de Vink, Boskoop, Netherlands, assignor to
The Conard-Pyle Company, West Grove, Pa.

Application October 18, 1935, Serial No. 45,672

1 Claim. (Cl. 47—61)

The present invention relates to a new and distinct variety of rose plant, having as its definite objective the production in a miniature rose of a novel and distinctive color.

To this end, in my own nursery I selected a plurality of miniature rose plants of a well known variety, commercially known as "Rouletti," and pollinated the flowers that were ripe with any pollen which I had at hand every day over a period of a number of days. The majority of these flowers were thus pollinated at least two or three times and often with different pollen. It may be noted, however, that in this process I used pollen of "Gloria Mundi"; that of a seedling climber of my own; also of F. J. Grootendorst, and of a yellow hybrid tea of unknown variety.

The seedling plant which I selected as a result of the foregoing procedure and which forms the subject matter of this origination had, to the best of my knowledge, for its male parent the "Gloria Mundi."

This new rose is a very attractive plant of its type and is quite different from either parent, both in respect to the plant and its flower in that the plant is smaller or more dwarfed than Rouletti or any other Polyantha and the flower adds a new color to the Rouletti type of miniature roses.

The drawing filed originally illustrates one of the mature plants of the new variety in actual size.

Asexual reproduction of the new variety both in the Netherlands and in the United States has proved the novel characteristics are perpetuated in the progeny.

The following is a detailed description of this new variety, all references to color applying to the Royal Horticultural Society's color chart:—

Parentage:
- Seed parent—Rouletti.
- Pollen parent—A Polyantha, probably Gloria Mundi.

Classification:
- Lawranceana.

*Flower*

Blooming habit:
- Continuous.

Bud:
- *Size.*—Tiny, ¼ inch long.
- *Form.*—Ovoid.
- *Color.*—Dark crimson (tone 4, plate 168).
- *Sepals.*—Branched with pointed ends. Stand out straight.
- *Calyx.*—Slender, about twice as long as wide.
- *Peduncle.*—Short, wiry but strong, light green, smooth.
- *Opening.*—Perfectly.

Bloom:
- *Size.*—¾ inch.
- *Borne.*—Singly and in clusters.
- *Stems.*—About one inch long.
- *Form.*—Flat, some blooms have 2 or 3 petaloids curled over the center almost hiding the stamens.
- *Permanence.*—Lasts several days.
- *Petalage.*—About 15.
- *Color.*—As it opens, face of the petal is dark crimson (tone 4, plate 168), with base of petal white; reverse same color but the white of the base extends further up on the petal. When ready to drop the shade is lighter but still the same color.

Petals:
- *Texture.*—Leathery.
- *Appearance.*—Inside lustrous, outside dull.
- *Form.*—Pear shaped except that tip has a blunt point.
- *Arrangement.*—Rather loosely formed.
- *Persistence.*—Drop off cleanly.
- *Fragrance.*—Very mild.
- *Lasting quality.*—Lasts until petals fall.

Genital organs:
- *Stamens, anthers.*—Very numerous. Color—yellow. Arrangement—even.
- *Stamens, filaments (threads).* — Various lengths. Color—white.
- *Pollen.*—Orange.
- *Styles.*—Bunched, uneven length, shorter than stamens.
- *Stigmas.*—Red.
- *Ovaries.*—Normal.

Fruit:
- Variety fertile with own pollen.
- *Form.*—Globular.
- *Aspect.*—Smooth.
- *Color at maturity.*—Orange.
- *Sepals.*—Stand out straight.

*Plant*

Form:
- Dwarf bush.

Growth:
- Bushy, nearly as wide as tall.

Foliage:
- *Number leaflets to compound leaf.*—5 on new, 7 on mature foliage.
- *Size.*—From ⅜-inch of side leaflets to ⅝-inch of tip leaflets; $\frac{7}{32}$-inch to $\frac{8}{32}$-inch wide at middle.

*Quantity.*—Abundant.

*Color.*—New foliage—bronzy light green. Mature foliage—light green above, pale green below.

*Shape.*—Long, narrow, pointed.

*Texture.*—Leathery upper side smooth between ribs, lower side rough.

*Edge.*—Serrated.

*Serration.*—Very even, not deep.

*Ribs and veins.*—Evenly ribbed, impressed, veined between ribs.

*Rachis.*—Color—light green, under side—prickly.

*Stipules.*—Short, serrated.

*Disease resistance.*—Unusually healthy, have not seen any disease on it.

Wood:

*New wood.*—Light green.

*Old wood.*—Light green.

Thorns:

No thorns or prickles, wood smooth.

I claim:

The new and distinct variety of rose plant shown and described, characterized by the distinctive color of its miniature flowers through all stages of their development, and the novelty of said color and the unusual dwarfish characteristic in this type of rose plants.

JOHN DE VINK.